(12) United States Patent
Miller

(10) Patent No.: US 10,508,985 B2
(45) Date of Patent: Dec. 17, 2019

(54) SYSTEMS AND METHODS FOR PUMP-PROBE SPECTROSCOPY

(71) Applicant: Northwestern University, Evanston, IL (US)

(72) Inventor: Stephen A. Miller, Wilmette, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 2 days.

(21) Appl. No.: 15/997,227

(22) Filed: Jun. 4, 2018

(65) Prior Publication Data

US 2019/0056313 A1 Feb. 21, 2019

Related U.S. Application Data

(60) Provisional application No. 62/515,386, filed on Jun. 5, 2017.

(51) Int. Cl.
| | |
|---|---|
| *G01N 21/25* | (2006.01) |
| *G01N 21/17* | (2006.01) |
| *G01N 21/39* | (2006.01) |
| *G01J 3/00* | (2006.01) |
| *G01N 21/63* | (2006.01) |
| *G01N 21/31* | (2006.01) |

(52) U.S. Cl.
CPC ............ *G01N 21/255* (2013.01); *G01J 3/00* (2013.01); *G01N 21/1717* (2013.01); *G01N 21/39* (2013.01); *G01N 21/636* (2013.01); *G01N 2021/1725* (2013.01); *G01N 2021/3125* (2013.01); *G01N 2201/0697* (2013.01); *G01N 2201/06113* (2013.01)

(58) Field of Classification Search
CPC ... G01N 21/636; G01N 21/637; G01N 21/638
See application file for complete search history.

(56) References Cited

U.S. PATENT DOCUMENTS

| | | | |
|---|---|---|---|
| 2009/0057536 A1* | 3/2009 | Hirose | G01J 1/04 250/208.1 |
| 2010/0091266 A1* | 4/2010 | Yasuda | G01N 21/3581 356/51 |

(Continued)

OTHER PUBLICATIONS

Berera et al., Ultrafast transient absorption spectroscopy: principles and application to photosynthetic systems, Photosynth Res 101, Jul. 4, 2009, pp. 105-118.

(Continued)

*Primary Examiner* — Shawn Decenzo
(74) *Attorney, Agent, or Firm* — Bell & Manning, LLC

(57) ABSTRACT

Pump-probe spectroscopy systems are provided. In an embodiment, such a system comprises an optical subsystem configured to generate a pulsed pump beam and a pulsed probe beam, the pulsed probe beam having a probe pulse frequency ω of at least 20 kHz; a detector subsystem configured to detect a sample signal induced by the pulsed pump beam and the pulsed probe beam; a chopper configured to adjust the frequency of the pump beam to ω/2, wherein the chopper is synchronized with a detector of the detector subsystem but is unsynchronized with the pulsed probe beam; and a data acquisition subsystem configured to initiate acquisition of image data by the detector based on a trigger signal derived from the pulsed pump beam.

15 Claims, 10 Drawing Sheets

(56) References Cited

U.S. PATENT DOCUMENTS

| | | | | |
|---|---|---|---|---|
| 2010/0195092 A1* | 8/2010 | Ohtake | ............. | G01B 11/0666 356/51 |
| 2011/0249253 A1* | 10/2011 | Nakanishi | ............ | G01N 21/552 356/51 |
| 2011/0273708 A1* | 11/2011 | Tong | ...................... | G01N 21/19 356/312 |
| 2012/0256104 A1* | 10/2012 | Hase | ................. | G11C 13/0004 250/492.1 |
| 2013/0129568 A1* | 5/2013 | Gusev | ................... | G01N 21/59 422/82.09 |
| 2014/0047908 A1* | 2/2014 | Sadri | ..................... | B01D 15/40 73/61.58 |
| 2014/0049768 A1* | 2/2014 | Sadri | ........................ | G01P 5/26 356/28 |
| 2015/0168347 A1* | 6/2015 | Sadri | ............... | G01N 27/44721 204/452 |
| 2017/0045440 A1* | 2/2017 | Devos | ................ | G01N 21/1702 |
| 2017/0059488 A1* | 3/2017 | Wolf | ................... | G01N 21/6486 |
| 2017/0152608 A1* | 6/2017 | Jin | ............................ | C30B 7/14 |
| 2017/0211977 A1* | 7/2017 | Jeys | ........................ | G01N 21/1717 |
| 2017/0219489 A1* | 8/2017 | Cheshnovsky | ........ | G02B 21/00 |
| 2017/0254749 A1* | 9/2017 | Yun | ...................... | A61B 5/0073 |

OTHER PUBLICATIONS

Polack et al., CO Vibration as a Probe of Ligand Dissociation and Transfer in Myoglobin, Physical Review Letters, vol. 93, No. 1, (2004).

Kanal et al., 100-kHz shot-to-shot broadband data acquisition for high-repetition-rate pump—probe spectroscopy, Optics Express, vol. 22, No. 14, Jul. 3, 2014, pp. 16965-16975.

T. Polak, Spectroscopie infrarouge impulsionnelle appliquee au transfert de ligands dans les hemoproteines, Thesis, Jan. 23, 2004.

* cited by examiner

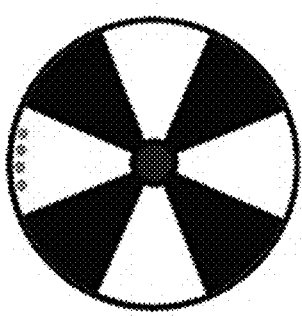
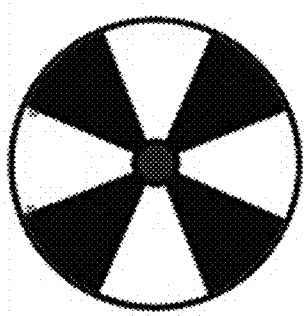
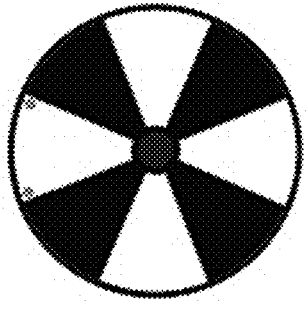
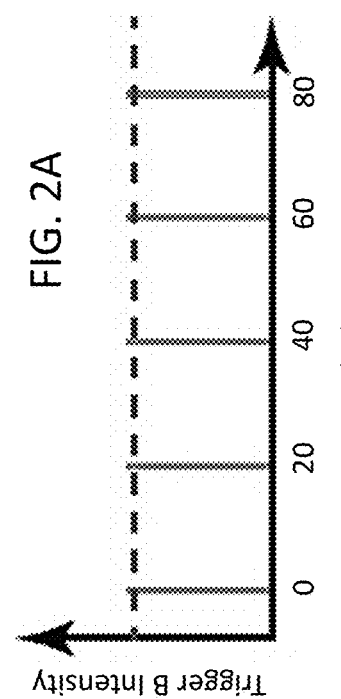
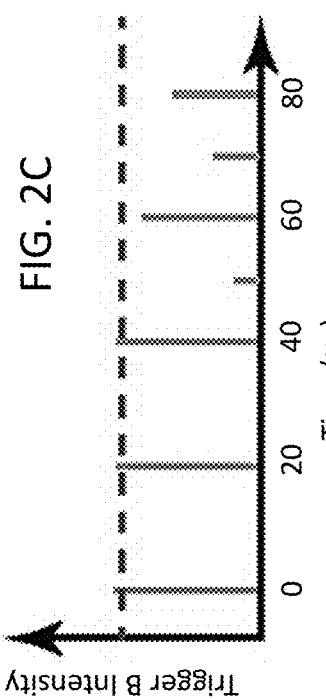
FIG. 2A  FIG. 2B  FIG. 2C

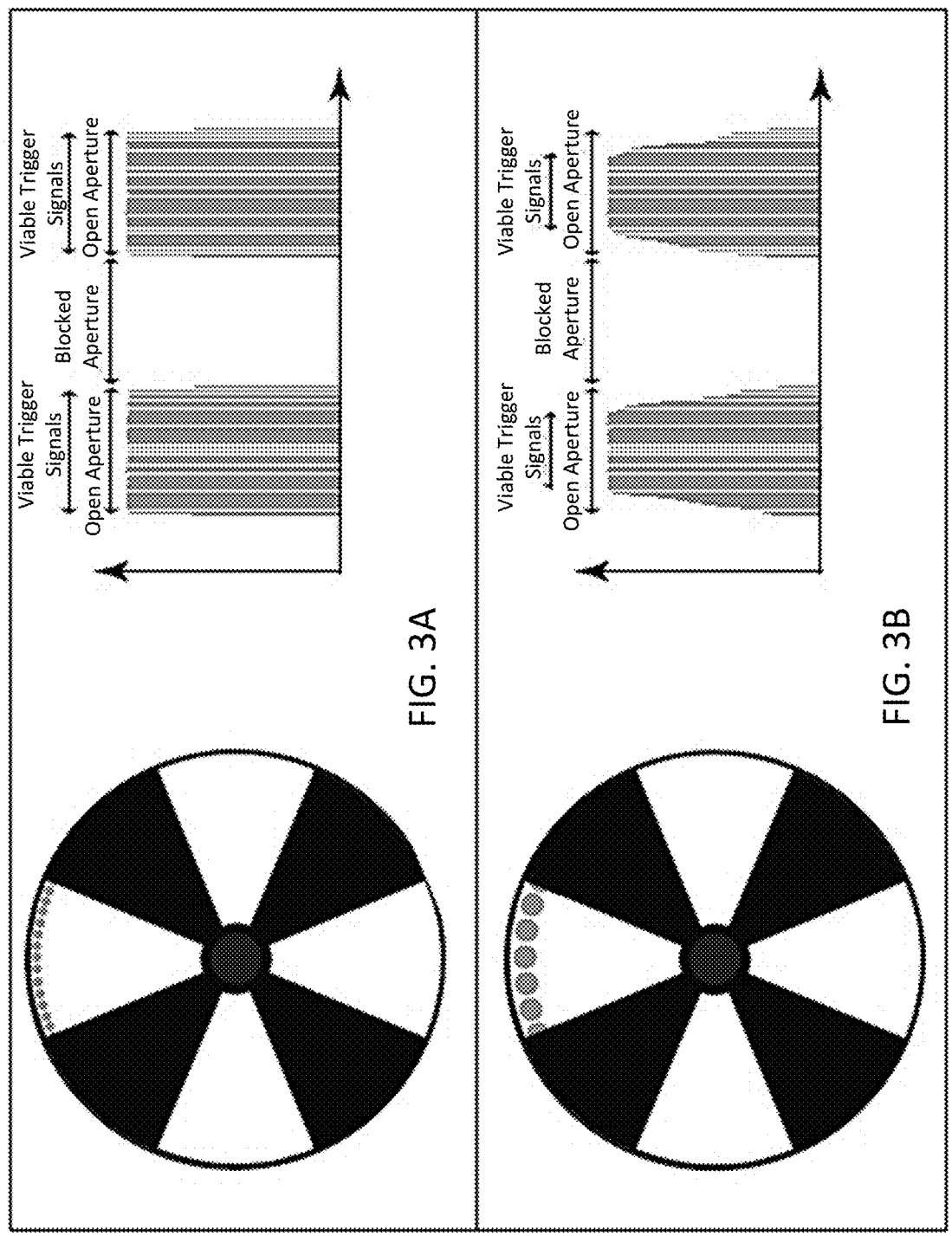

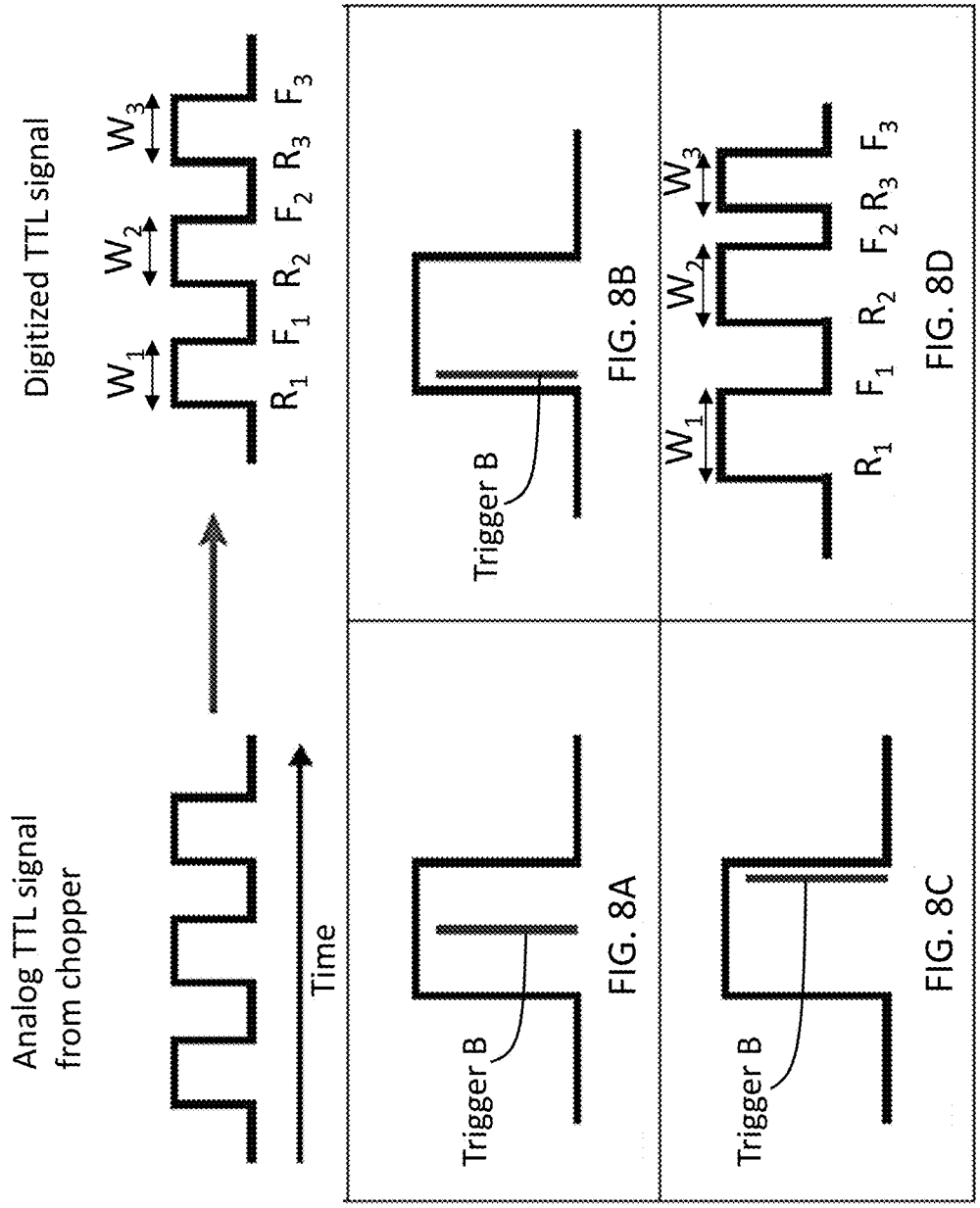

SYSTEMS AND METHODS FOR PUMP-PROBE SPECTROSCOPY

CROSS-REFERENCE TO RELATED APPLICATIONS

The present application claims priority to U.S. Provisional Patent Application No. 62/515,386 that was filed Jun. 5, 2017, the entire contents of which are hereby incorporated by reference.

REFERENCE TO GOVERNMENT RIGHTS

This invention was made with government support under N00014-11-1-0729 awarded by the Office of Naval Research. The government has certain rights in the invention.

BACKGROUND

In pump probe spectroscopy shot to shot detection is the ideal method of acquiring data as it takes advantage of the strong intensity correlations that exist between laser pulses that are close together in time. The further apart the pulses are in time, the worse the correlations become, and as a result, the data becomes noisier. Shot to shot differencing has been widely used at normal laser repetition rates (i.e., a few kHz), but becomes much more difficult at higher repetition rates. The primary reason for this is that the "pump" laser beam needs to be modulated (i.e., blocked) at exactly half the repetition rate of the "probe" laser beam. At slow laser repetition rates (~5 kHz or lower), this can be done with a mechanical chopper. At higher repetition rates (e.g., 100 kHz), however, the moment of inertia of the spinning chopper blade becomes sufficiently high that it is challenging for the blade to be synchronized to the laser output pulse train.

SUMMARY

Provided are pump-probe spectroscopy systems and related methods.

Pump-probe spectroscopy systems are provided. In an embodiment, such a system comprises an optical subsystem configured to generate a pulsed pump beam and a pulsed probe beam, the pulsed probe beam having a probe pulse frequency $\omega$ of at least 20 kHz; a detector subsystem configured to detect a sample signal induced by the pulsed pump beam and the pulsed probe beam; a chopper configured to adjust the frequency of the pump beam to $\omega/2$, wherein the chopper is synchronized with a detector of the detector subsystem but is unsynchronized with the pulsed probe beam; and a data acquisition subsystem configured to initiate acquisition of image data by the detector based on a trigger signal derived from the pulsed pump beam.

In another embodiment, a pump-probe spectroscopy system comprises a processor; and a non-transitory computer-readable medium comprising instructions, that, when executed by the processor, cause the system to receive a first trigger signal derived from a pulsed probe beam having a probe pulse frequency $\omega$ and output the first trigger signal to a detector; receive a second trigger signal derived from a pulsed pump beam having a pump pulse frequency $\omega/2$, the second trigger signal operably coupled to the detector; determine if the second trigger signal meets or exceeds a predetermined threshold value; and initiate acquisition of image data by the detector if the second trigger signal meets or exceeds the predetermined threshold value.

Non-transitory computer-readable media for the pump-probe spectroscopy systems are also provided. In an embodiment, such a medium comprises instructions, that, when executed by a processor, cause a pump-probe spectroscopy system to receive a first trigger signal derived from a pulsed probe beam having a probe pulse frequency $\omega$ and output the first trigger signal to a detector; receive a second trigger signal derived from a pulsed pump beam having a pump pulse frequency $\omega/2$, the second trigger signal operably coupled to the detector; determine if the second trigger signal meets or exceeds a predetermined threshold value; and initiate acquisition of image data by the detector if the second trigger signal meets or exceeds the predetermined threshold value.

Methods for performing pump-probe spectroscopy are also provided. In an embodiment, such a method comprises receiving, by a processor, a first trigger signal derived from a pulsed probe beam having a probe pulse frequency $\omega$ and outputting the first trigger signal to a detector; receiving, by the processor, a second trigger signal derived from a pulsed pump beam having a pump pulse frequency $\omega/2$, the second trigger signal operably coupled to the detector; determining, by the processor, if the second trigger signal meets or exceeds a predetermined threshold value; and initiating acquisition of image data by the detector if the second trigger signal meets or exceeds the predetermined threshold value.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

As shown in FIG. 1, Trigger A records the timing of amplifier pulse train and is sent to a frame grabber card (National Instruments PCIe 1430) installed on a PC. This in turn sends the trigger signal to the fast array detector (E2V AViiVA® µM4) which synchronizes the detector acquisition to the laser. The probe beam is created and directed onto a mechanical delay stage in order to delay it relative to the pump beam. Subsequently, it is directed onto the sample and then into a spectrometer, which disperses it spectrally onto the array detector. Simultaneously, the pump beam is directed through an unsynchronized high speed optical chopper (Scitec Instruments 310CD, 300D445 wheel) turning at half the repetition rate of the laser. Because the slot dimensions in the chopper are quite small (0.34 mm), the beam is focused tightly at the plane of the chopper wheel, to allow ~100% transmission of the pump beam when the chopper is in the unblocked phase. After the chopper, a small fraction of the pump beam is redirected off a coverslip, through a variable attenuator, and onto an inexpensive photodiode. The majority pump fraction is directed to photoexcite the sample. The electrical pulses (Trigger B) from the photodiode are sent to the PC/frame grabber which triggers the start of an acquisition of a sequence of 1,100 sequential images (i.e., an acquisition event). Because the chopper is unsynchronized, it is continuously walking in and out of phase with the laser. Therefore, the pump fraction incident onto the photodiode is attenuated such that only fully unblocked pump pulses are intense enough to trigger the start of the sequence acquisition. (See FIGS. 2A-2C.) Consequently, the phase of the chopper is always constant at the start of each acquisition event (i.e. unblocked), and because the acquisition time of a sequence of 1,100 images at ~100 kHz is only a few milliseconds, the chopper does not have enough time to walk out of phase. To acquire more images, the frame grabber simply waits till the next Trigger B signal and acquires another set of sequential images. Note that for the embodiment of FIG. 1, 1,100 was empirically determined to be the ideal number of images in an acquisition event as it is the best compromise between keeping the time of an acquisition event short while acquiring an overall large number of images.

FIGS. 2A-2C show schematics of Trigger B signal trains for a 100 kHz laser and their corresponding starting chopper phase positions. Note that this schematic is not indicative of how many slots are actually in the chopper wheel (e.g., 445), but it does approximately show the relative sizes of the fully focused beam and chopper aperture. (See FIGS. 3A-3B for more details.) The dashed line indicates the detector trigger threshold (i.e., predetermined threshold value) for starting the acquisition of an image sequence (i.e., an acquisition event). The variable attenuator shown in FIG. 1 is set so that a fully unblocked pump pulse is just be intense enough to generate a trigger signal above this threshold. Because the chopper is unsynchronized to the laser and because high speed mechanical choppers inherently have a large amount of phase jitter, there are three possible starting chopper phase positions to consider. In FIG. 2A, the phase of the chopper is such that the first pump pulse in the 1,100-pulse sequence passes through away from the edges of the aperture. The timescale of the acquisition event (e.g., 11 ms) is short enough such that the phase drift is too slow to become an issue. Thus, the pump pulse sequence is modulated perfectly at 50 kHz. In FIG. 2B, the phase of the chopper is such that the pump pulse is partially clipped. The portion of the pump pulse that is transmitted is not intense enough to generate a trigger above the threshold. Nothing happens in this case, i.e., an acquisition event is not triggered. In FIG. 2C, the phase of the chopper is such that the first pump pulse in the 1,100 pulse sequence passes through very close to the edge of the aperture. In this situation, chopper phase drift can become relevant over an 11 ms acquisition time and the pump pulse train is not perfectly modulated across the entire 1,100 pulse sequence. Mostly this manifests itself as a reduction in overall signal intensity, but it can also affect the spectral signal if either the pump or probe beams are spatially/chromatically chirped. In either case, it is advantageous to ignore this data, and as further described below, an efficient real-time algorithm may be utilized to discard bad image sequences that are collected when the pump beam is poorly modulated. For the illustrative system shown in FIG. 1, it has been determined that about 92.5±5% of image sequences collected are in the situation depicted in FIG. 2A, and 7.5% are in the situation depicted in FIG. 2C. Also, further described below, is a real-time algorithm to prevent the acquisition of "bad image sequences," i.e., those associated with a nonoptimal chopper phase (e.g., FIG. 2C).

FIGS. 3A-3B show the effect of the focused pump beam spot size on Trigger B timing. Note that although the relative sizes of the aperture and focused spot size are approximately to scale, the number of apertures in the chopper blade shown here is not indicative of the actual chopper. As shown in FIG. 3A, when the pump is focused tightly relative to the chopper aperture size, the system becomes more binary. That is, the pump beam is, for the most part, either fully blocked or fully unblocked. This can be seen on the right side of the figure, which schematically shows what one observes if the photodiode Trigger B signal is sampled many times (e.g., with an oscilloscope). When the spot size is small, the sequence of unblocked and blocked regions appears almost as a square wave. This is because a pump pulse can be fully transmitted even when it passes very close to the edge of the open chopper aperture. As shown in FIG. 3B, if the spot size is increased, the pump pulse cannot be as close to the edge of the open aperture without being partially clipped. The oscilloscope signal in this case would be flat in the middle of the open aperture and would show a Gaussian fall off (assuming a Gaussian beam profile) as the pump beam nears the edge of the aperture and starts to become partially clipped. The width of the Gaussian falls off in time/chopper phase space is linearly dependent on the spot size diameter of the pump.

In practice this effect can be used as a filter to ensure that the start of an image sequence acquisition occurs only when the center of a pump pulse is away from the edge of the aperture. That is, only when the pump is fully transmitted creating a photodiode signal that is just above the trigger threshold. As one saw in FIG. 2A, this is the most advantageous situation. However, one might expect that this filtering effect would not make much of a difference to the overall quality of the pump modulation because as the focused pump spot diameter increases, the chopper phase window in which the beam will be fully transmitted becomes smaller.

Thus, a relatively small phase drift during the course of a sequence acquisition could still result in some partially clipped pump pulses. Intuitively, one might expect that these two effects would cancel themselves out, but this is not exactly the case. The percentage of pump pulse trains that are perfectly modulated is slightly higher (i.e. 92.5±5%) when the beam is not tightly focused. This suggests that the rate of chopper phase drift is slightly faster near the edges of the phase jitter range than in the center. Therefore, it still more advantageous for the pump pulse that triggers a sequence acquisition to pass through the center of the open aperture even when it has a relatively large focused spot size. As one increases the spot size further, this advantage will diminish when the focused spot size nears the size of the chopper aperture. For the illustrative system shown in FIG. 1, it was determined that a focused diameter of ~50 micrometers is ideal with the chopper used (Scitec Instruments 310CD, 300D445 blade).

Figure 1:
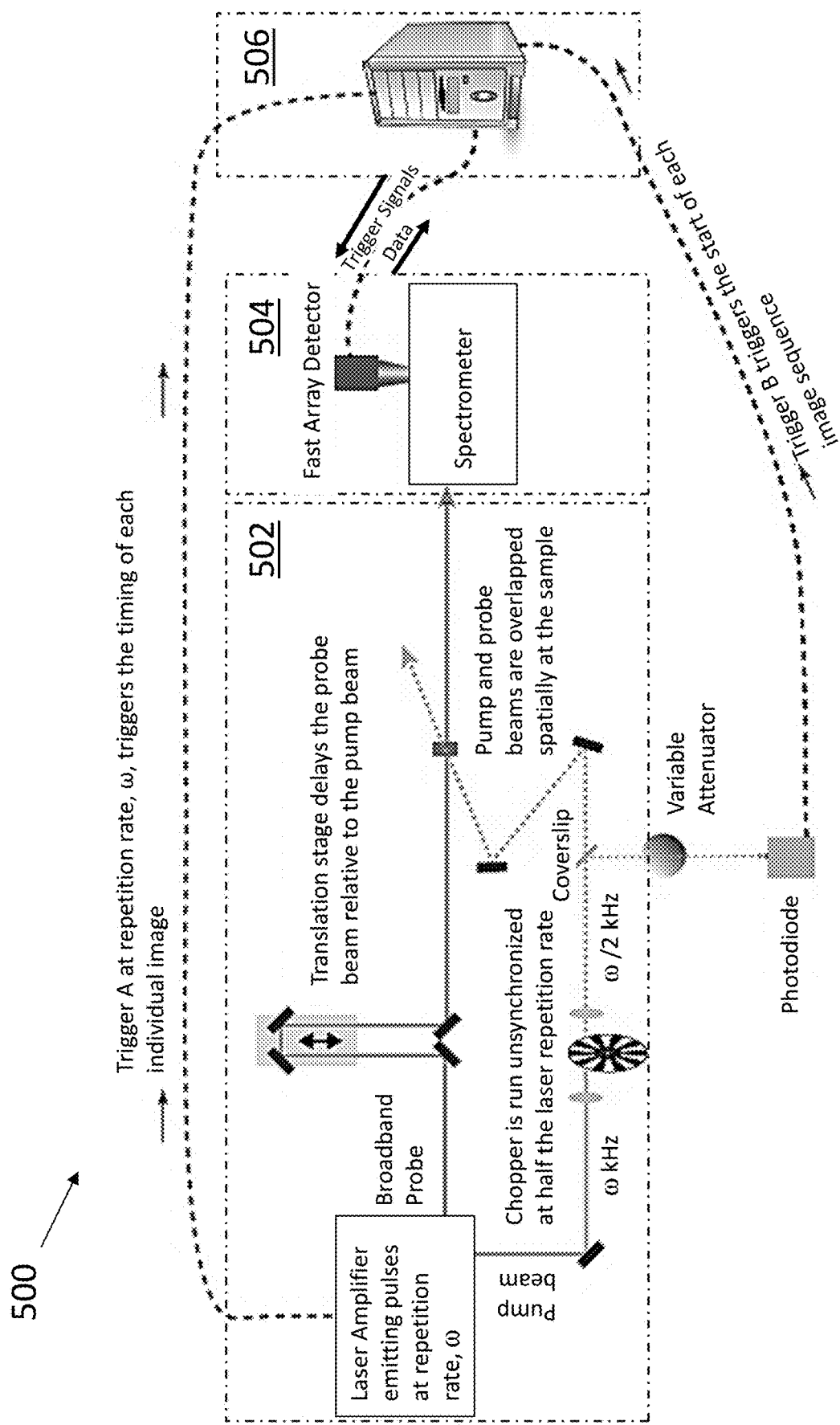
FIG. 1 is a schematic depicting an experimental setup for a $\omega$ kHz (e.g., 100 kHz) shot to shot pump-probe experiment according to an illustrative embodiment. The example shown here is for a typical femtosecond transient absorption experiment, but the beam chopping/triggering/acquisition technique is viable for any ~100 kHz pump-broadband probe experiment. Noted that for simplicity, only the laser amplifier is shown. In a real experiment, optics subsequent to the laser amplifier (e.g., optical parametric amplifier, supercontinuum generation, etc.) may be present to convert the laser fundamental into the desired pump and probe beams. The exact optical techniques and optical components depend upon the type of pump-probe experiment.
Figure 4A:
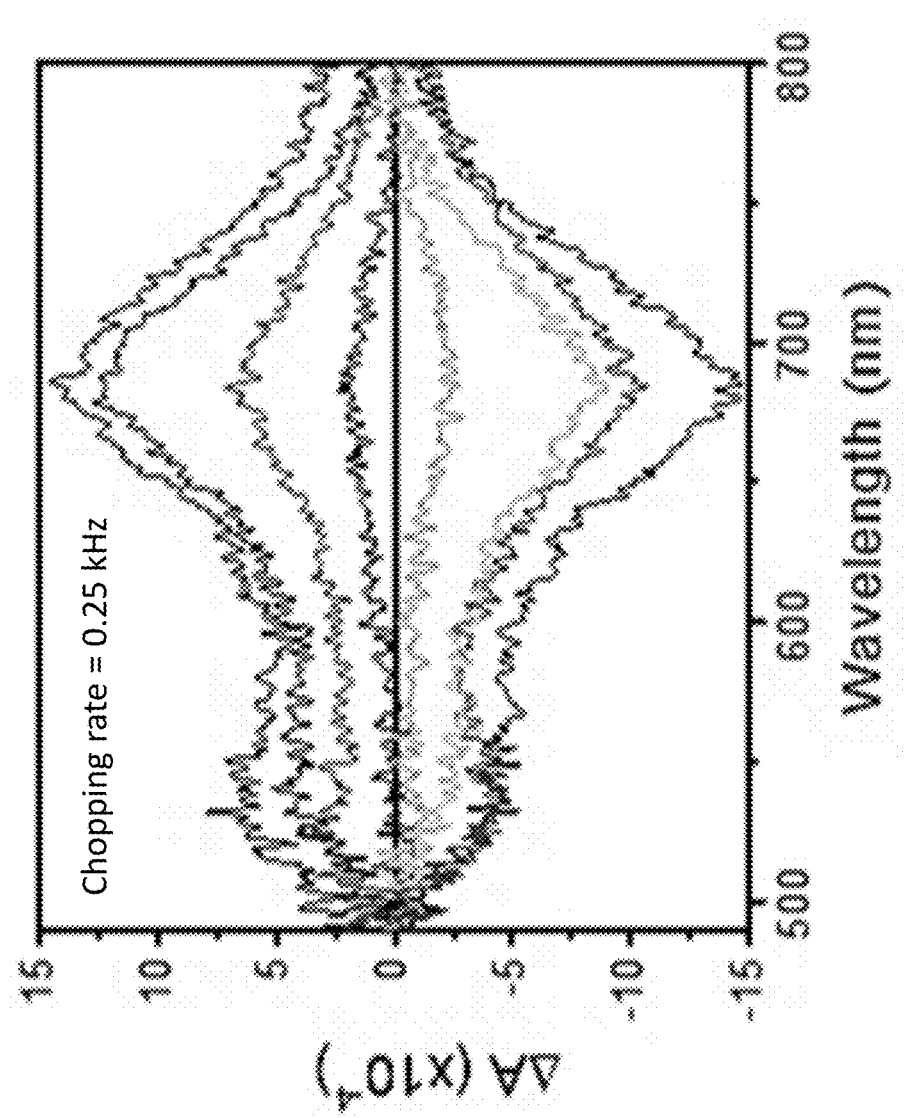
Figure 4B:
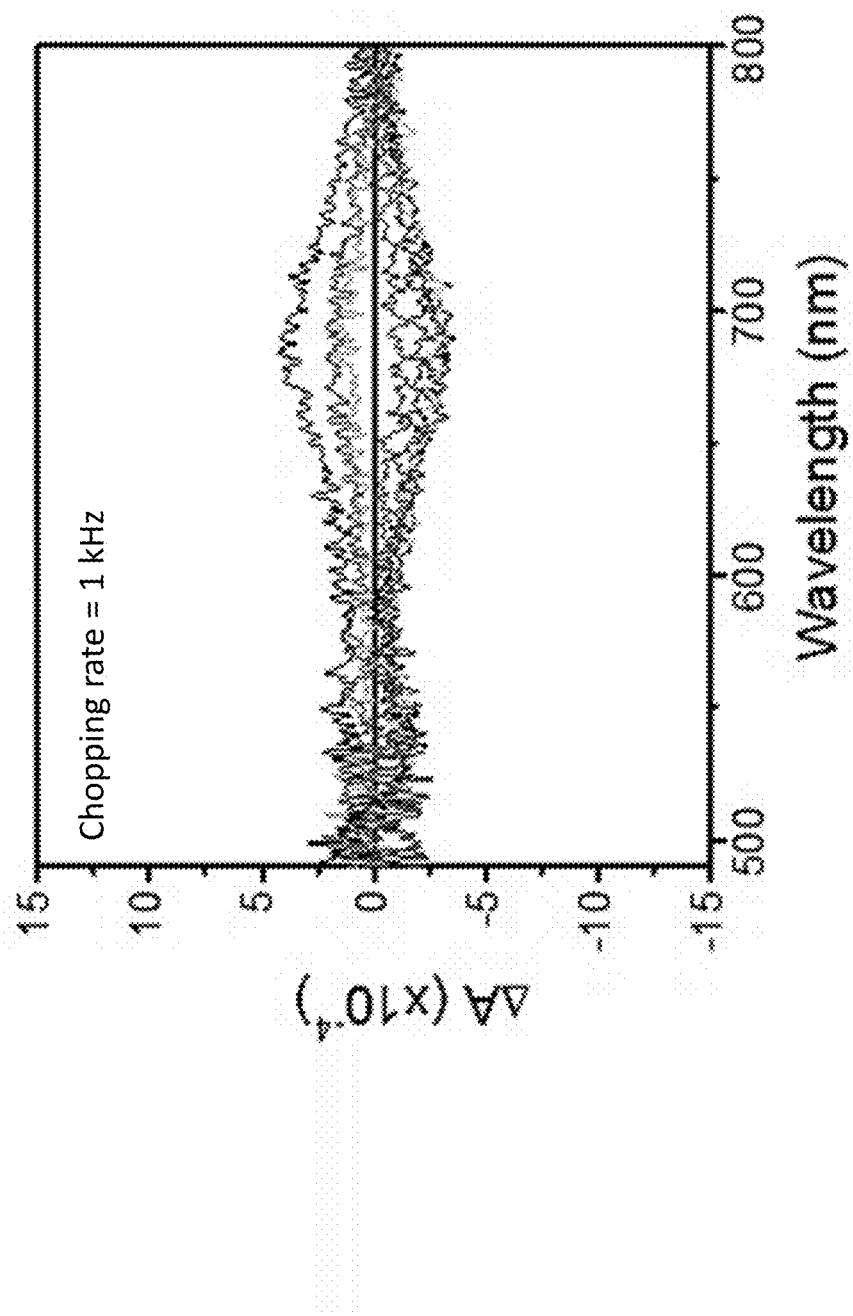
Figure 4C:
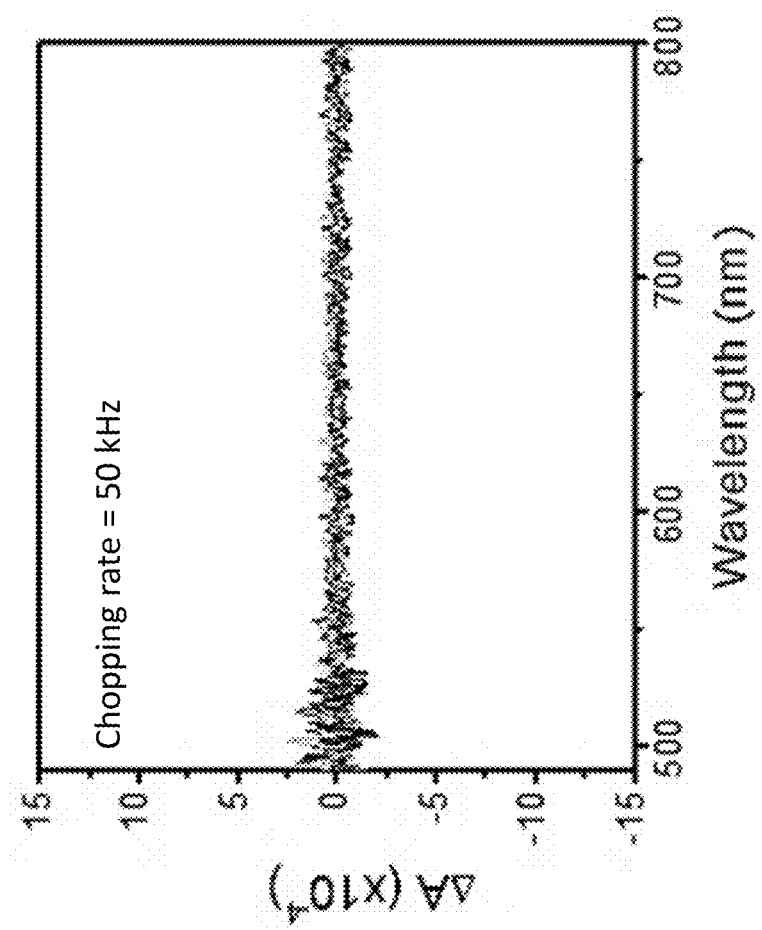

FIGS. 4A-4C shows Example baseline transient absorption data taken with a 100 kHz laser using the system of FIG. 1 when acquired at various chopping rates (i.e., the different curves in each figure correspond to different chopping rates. Each spectrum shown is calculated from a single 1,100 image sequence (i.e., a single acquisition event). Note that the pump pulse was blocked prior to the sample for these experiments; therefore, a perfectly flat baseline should, in theory, be observed. FIGS. 4A and 4B represent conventional chopping speeds of 0.25 kHz and 1 kHz, respectively; therefore, badly correlated probe pulses that exist on the chopping timescale result in large fluctuations in the baseline. These fluctuations are significantly above the observed electronic noise level and will significantly diminish the overall signal to noise. FIG. 4C (50 kHz) is modulated at half the repetition rate of the laser and thus compares strongly correlated probe pulses. As a result, there is almost no baseline fluctuation observed, and one is left only with the electronic noise.

Figure 5:
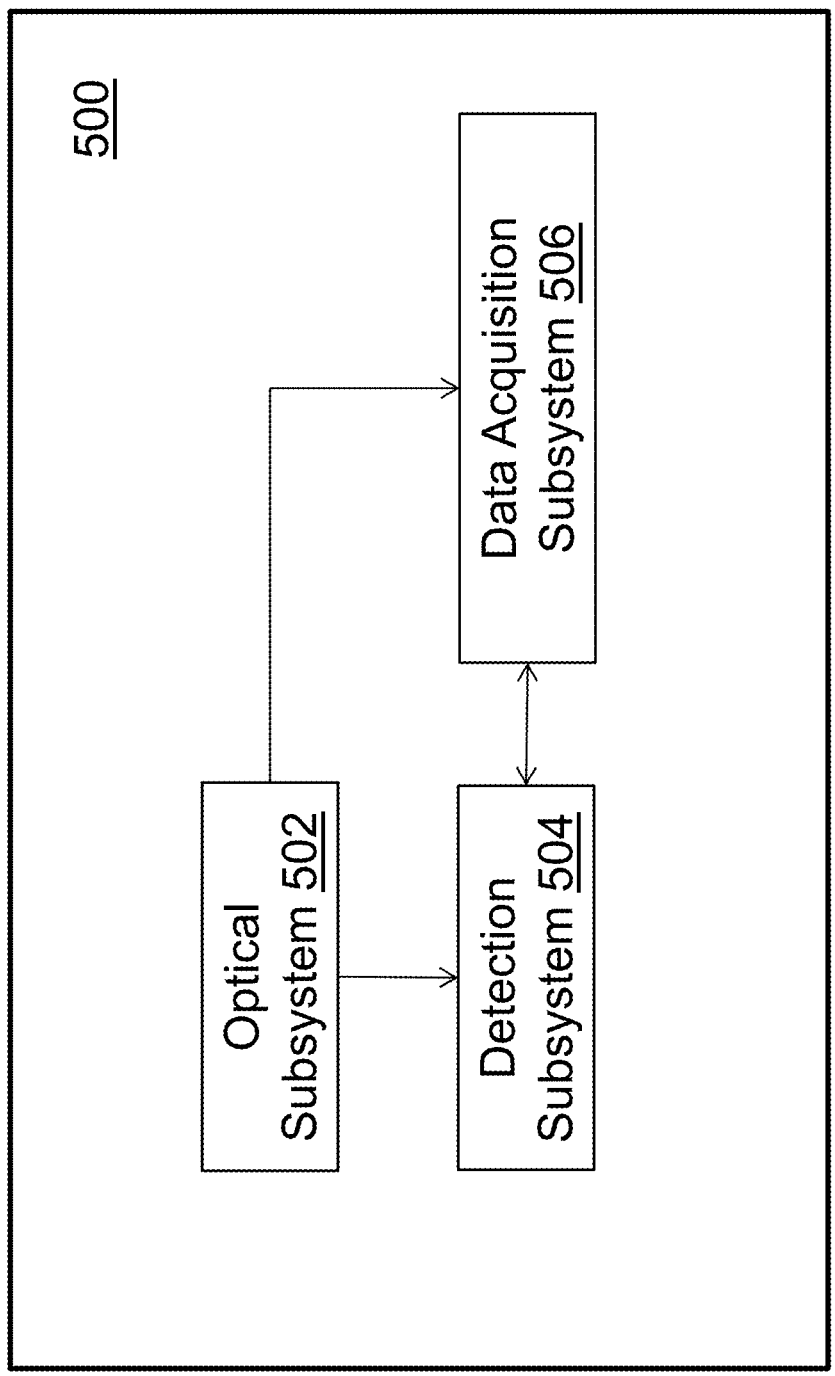

FIG. 5 depicts a block diagram of a pump-probe spectroscopy system according to an illustrative embodiment. FIG. 1 is an illustrative embodiment of the block diagram of FIG. 5.

Figure 6:
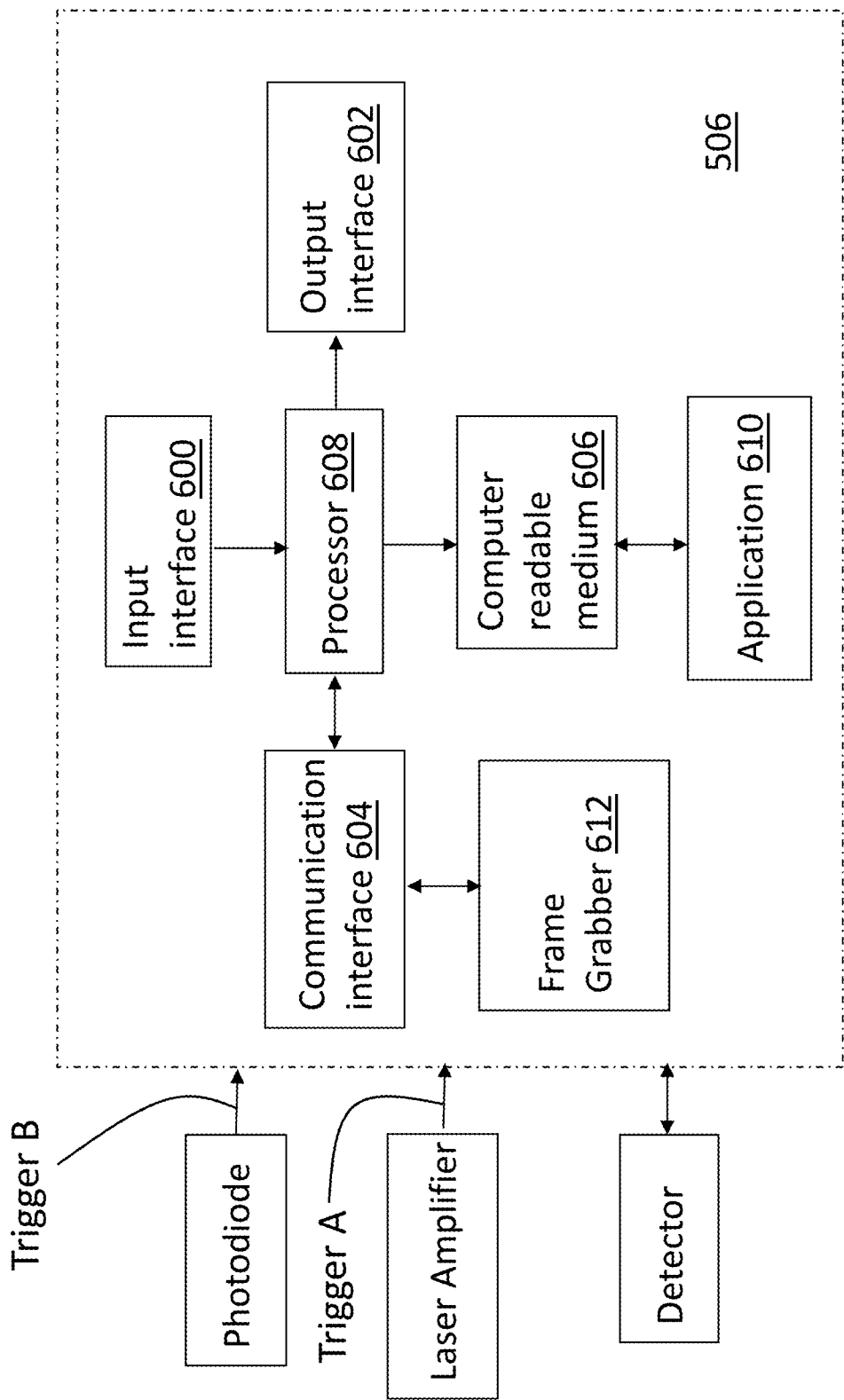

FIG. 6 depicts a block diagram of a data acquisition subsystem of the pump-probe spectroscopy system of FIG. 5 according to an illustrative embodiment.

Figure 7:
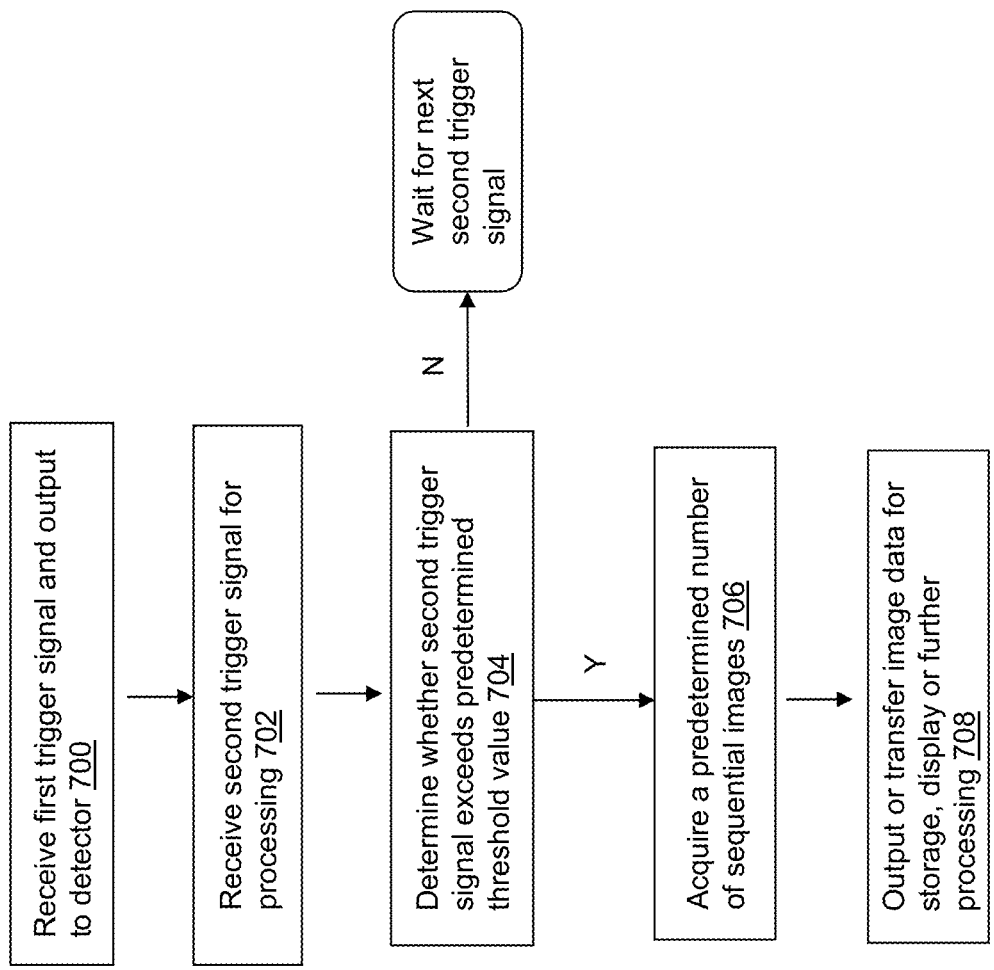

FIG. 7 depicts a flow diagram illustrating example operations performed by an application of the data acquisition subsystem of FIG. 6 according to an illustrative embodiment.

FIGS. 8A-8D depict a technique for preventing the acquisition of "bad image sequences," i.e., those associated with a nonoptimal chopper phase (e.g., FIG. 2C). In the top panel, an analog TTL signal from the "sync-out" port on the chopper is converted to a digitized TTL signal using a data acquisition device (DAQ). The analog/digitized TTL signal corresponds to the chopper phase. The rise and fall of the digitized TTL signal are indicated with "R" and "F," respectively; the width is indicated with "W." In FIG. 8A, the trigger signal from the photodiode monitoring the pump beam (Trigger B signal) arrives at the center of the digitized TTL signal. This is an optimal situation and so the trigger signal is accepted. In FIGS. 8B, 8C, the trigger signal arrives close to the rise (FIG. 8B) and fall (FIG. 8C) of the digitized TTL signal. This is a nonoptimal situation and so the trigger signals are rejected. In FIG. 8D, the time gap between the rises and falls (i.e., the width) of the digitized TTL signal is rapidly changing, indicating a drift in chopper speed. This is another nonoptimal situation and so the trigger signals over this time period are rejected.

DETAILED DESCRIPTION

Provided are pump-probe spectroscopy systems and related methods. The systems and methods may be used to achieve shot-to-shot differencing with high efficiency (e.g., 100%) without requiring expensive electronics or complicated triggering methods. By shot-to-shot differencing it is meant that data is captured from every probe laser pulse in a pulse sequence and then compared to the next pulse in the sequence.

FIG. 5 shows a block diagram of a pump-probe spectroscopy system 500. The system 500 comprises an optical subsystem 502, a detection subsystem 504 and a data acquisition subsystem 506. An illustrative embodiment of the pump-probe spectroscopy system 500 is shown in FIG. 1, as is further described below. The pump-probe spectroscopy system and each of its subsystems may comprise fewer or additional components. In addition, the designation of the subsystems shown in FIG. 5 and of the components of the subsystems shown in FIG. 1 is not intended to be limiting. By way of illustration, components of a particular subsystem may be considered to be components of another subsystem and still provide the desired functionality to the pump-probe spectroscopy system 500.

The optical subsystem 502 is configured to generate a pump beam and a probe beam and to induce an optical signal from a sample of interest upon illuminating the sample with the probe and pump beams. The probe beam may be a pulsed probe beam characterized by a probe pulse frequency $\omega$. The probe pulse frequency may be relatively high, e.g., at least 20 kHz, at least 100 kHz, in the range of from about 20 kHz to about 100 kHz. The probe beam may be a broadband probe beam characterized by a relatively broad optical bandwidth, e.g., 500 nm or more. The broadband probe beam may comprise wavelengths across various ranges, e.g., from about 400 nm to about 1100 nm, depending upon the pump-probe spectroscopic technique and the sample of interest. The pump beam may also be pulsed, characterized by a pump pulse frequency. The pump pulse frequency may be half of the probe pulse frequency, $\omega/2$. The pump beam may be characterized by a pump wavelength, which may be fixed or tunable over a desired range of wavelengths.

The optical subsystem 502 may include a variety of components (e.g., optical, mechanical, electrical and multifunctional components) depending upon the desired pump-probe spectroscopic technique and to achieve the pump and probe beam characteristics described above. For generating the pump and probe beams, components may include various combinations of an oscillator, an amplifier, supercontinuum generator, optical parametric amplifier, optical parametric generator, sum frequency generator, and second harmonic generator. Components may include various beam directing and beam shaping elements (e.g., mirrors, lenses, beamsplitters, etc.) for directing/shaping the pump and probe beams and to provide the desired configuration at the sample (e.g., beams intersecting at the sample at a predetermined angle). Components may include a chopper (e.g., a mechanical chopper) for blocking pulses of the pump pulse to generate the desired pump pulse frequency. The desired pump pulse frequency may be set by using the chopper's internal clock drive.

FIG. 1 depicts illustrative components for an illustrative embodiment of pump-probe spectroscopic system 500, including an illustrative embodiment of the optical subsystem 502. This figure makes clear that the chopper is not synchronized with the laser amplifier (and vice versa, i.e., the laser amplifier is not synchronized with the chopper). Thus, the chopper may be referred to as an "unsynchronized chopper" or an "asynchronous chopper." This means that during the normal operation of the pump-probe spectroscopy system 500, the phase of chopper and the phase of the probe beam will drift randomly relative to one another to become out-of-phase. Again, the outline encompassing the components of the optical subsystem 502 shown in FIG. 1 is not intended to be limiting. By way of illustration, the coverslip, variable attenuator and photodiode could be considered to be part of the data acquisition subsystem 506.

The detection subsystem 504 is configured to detect the sample signal induced by the optical subsystem 502. The detection subsystem 504 may include a variety of components depending upon the desired pump-probe spectroscopic technique and the nature of the sample signal. Components may include a spectrometer for spectrally dispersing the sample signal (e.g., separating the sample signal into its component wavelengths) and a detector for collecting the dispersed sample signal as an image (e.g., a spectrally and temporally resolved image). Various spectrometers and detectors may be used. The detector, however, is one capable of collecting the dispersed sample signal at least as fast as the probe pulse frequency. FIG. 1 depicts illustrative components for an illustrative embodiment of the detection subsystem 504. Again, the outline encompassing the components of the detection subsystem 504 is not intended to be limiting.

The data acquisition subsystem 506 is configured to control the detector of the detection subsystem 504 to acquire image data for, e.g., storage, display, and/or further processing. An illustrative embodiment of the data acquisition subsystem 506 is shown in FIG. 6. The data acquisition subsystem 506 may include an input interface 600, an output interface 602, a communication interface 604, a computer-readable medium 606, a processor 608, and an application 610.

The input interface 600 provides an interface for receiving information into the data acquisition subsystem 506. The input interface 600 may interface with various input technologies including, but not limited to, a keyboard, a display, a mouse, a track ball, a keypad, one or more buttons, etc. to allow the user to enter information into the data acquisition subsystem 506 or to make selections presented in a user interface displayed on the display. The data acquisition subsystem 506 may have one or more input interfaces that use the same or a different interface technology. Display, keyboard, etc. further may be accessible by the data acquisition subsystem 506 through the communication interface 604.

The output interface 602 provides an interface for outputting information from the data acquisition subsystem 506. For example, the output interface 602 may interface with various output technologies including, but not limited to, the display, a printer, etc. The data acquisition subsystem 506 may have one or more output interfaces that use the same or a different interface technology. The printer, etc. further may be accessible by the data acquisition subsystem 506 through the communication interface 604.

The communication interface 604 provides an interface for receiving and transmitting data between devices using various protocols, transmission technologies, and media. The communication interface 604 may support communication using various transmission media that may be wired or wireless. The data acquisition subsystem 506 may have one or more communication interfaces that use the same or a different communication interface technology. Signals, data, etc. may be transferred between the data acquisition system 506 and the other subsystems or components of the pump-probe spectroscopy system 500 using the communication interface 604. By way of illustration, as shown in FIG. 1, this includes receipt of a first trigger signal ("Trigger A") from a component of the optical subsystem 502. Trigger A may be the master clock trigger signal from the synchronization out port on the laser amplifier or a signal derived from an external photodiode optically coupled to the probe beam. This further includes receipt of a second trigger signal ("Trigger B") from a photodiode optically coupled to the pump beam. This further includes transmission of the first and second trigger signals to the detector of the detection subsystem 504. With reference back to FIG. 6, the data acquisition subsystem 506 may further include a frame grabber 612 operably coupled to the detector of the detection subsystem 504 via the communication interface 604.

The computer-readable medium 606 is an electronic holding place or storage for information so that the information can be accessed by the processor 608. The computer-readable medium 606 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. The data acquisition subsystem 506 may have one or more computer-readable media that use the same or a different memory media technology.

The processor 608 executes instructions which may be carried out by a special purpose computer, logic circuits, or hardware circuits. Thus, the processor 608 may be implemented in hardware, firmware, or any combination of these methods and/or in combination with software. The term "execution" is the process of running an application or the carrying out of the operation called for by an instruction. The instructions may be written using one or more programming languages, scripting languages, assembly languages, etc. The processor 608 executes an instruction, meaning that it performs/controls the operations called for by that instruction. The processor 608 operably couples with the input interface 600, with the output interface 602, with the computer-readable medium 606, and with the communication interface 604 to receive, to send, and to process information. The processor 608 may retrieve a set of instructions from a permanent memory device and copy the instructions in an executable form to a temporary memory device that is generally some form of RAM. The data acquisition subsystem 506 may include a plurality of processors that use the same or a different processing technology.

The application 610 performs operations associated with controlling the detector of the detection subsystem 504 to acquire image data. Some or all of the operations described herein may be embodied in the application 610. The operations may be implemented using hardware, firmware, software, or any combination of these methods. In the illustrative embodiment of FIG. 1, the application 610 is implemented in software (comprised of computer-readable and/or computer-executable instructions) stored in computer-readable medium 606 and accessible by processor 608 for execution of the instructions that embody the operations of the application 610. The application 610 may be written using one or more programming languages, assembly languages, scripting languages, etc.

With reference to FIG. 1, the pump-probe spectroscopy system 500 may include additional components, including components configured to generate the second trigger signal ("Trigger B"). Illustrative such components include a coverslip (or the like) configured to reflect a portion of the pump beam to a variable attenuator (or the like) configured to reduce the power/intensity of the pump beam to a predetermined attenuation value. The predetermined attenuation value may be selected so that a fully unblocked pump pulse (i.e., pump pulse not blocked by the chopper) has a power/intensity that matches a predetermined threshold value (further described below) associated with the data acquisition subsystem 506 (e.g., the frame grabber 612). (This matching condition is illustrated in FIG. 2A.) The attenuated pump beam is incident upon a photodiode (or the like), which converts the pump beam to an electrical signal, i.e., the second trigger signal.

As shown in FIG. 1, the optical subsystem 502 may also include lenses (or the like) before and after the chopper in order to focus the pump beam onto the plane of the chopper and to recollimate the pump beam after passing through the chopper, respectively. The lens prior to the chopper focuses the pump beam to a focal spot size. The focal spot size may be selected to allow the entire pump beam to be transmitted through an aperture of the chopper when the pump beam is centered in that aperture. The particular focal spot size may also be selected to maximize the number of pump pulses which are perfectly modulated (see FIG. 3A). However, as discussed in the Example below with reference to FIG. 3A, the optimal focal spot size may be greater than the minimum focal spot size achievable with the selected lens.

Various subsystems (and their components) of the pump-probe spectroscopy system 500, e.g., the detection system 504 and the data acquisition subsystem 506, may be integrated into a single device or their functionality may be distributed across one or more devices that are connected directly or through a network that may be wired and/or wireless. In the illustrative embodiment of FIG. 1, the detector of the detection system 504 is connected to the data acquisition system 506 using a cable for transmitting information.

With reference to FIG. 7, exemplary operations associated with the application 610 are described. Additional, fewer, or different operations may be performed depending on the embodiment. The order of presentation of the operations of FIG. 7 is not intended to be limiting. Thus, although some of the operational flows are presented in sequence, the various operations may be performed in various repetitions, concurrently, and/or in other orders than those that are illustrated.

In an operation 700, a first trigger signal (e.g., "Trigger A") is received from the optical subsystem 502 (e.g., by the frame grabber 612 of the data acquisition system 506), and output to the detector of the detection system 504. This synchronizes the detector to the probe beam so that individual images may be acquired only when the sample is illuminated with the probe beam.

In an operation 702, a second trigger signal (e.g., "Trigger B") is received from the photodiode (e.g., by the frame grabber 612) for processing by the processor 608.

In an operation 704, a determination is made whether the received second trigger signal exceeds a predetermined threshold value. If the received second trigger signal exceeds the predetermined threshold value (i.e., the determination is Yes), the second trigger signal is accepted (e.g., by outputting the signal to the detector of the spectral detector system 504) to initiate an acquisition event, i.e., the acquisition of a predetermined number of sequential images by the detector, in an operation 706. The predetermined number may vary, depending in part on the selected probe pulse frequency and the selected chopper. However, the predetermined number may be selected to maximize the number of acquired images before the chopper (and thus the pump beam) and the probe beam become out-of-phase. If the received second trigger signal does not exceed the predetermined threshold value (i.e., the determination is No), the second trigger signal is rejected (i.e., by not outputting the second trigger signal). Then, the data acquisition subsystem 506 waits for the next second trigger signal from the photodiode.

In an operation 708, the acquired image data is output or transferred for storage, display, and/or further processing.

The operations of FIG. 7 or certain operations thereof may be repeated at the same set of experimental conditions (e.g., same time delay between the pump and probe beams) or at a different set of experimental conditions (e.g., different time delay). Further processing may be accomplished by the data acquisition system 506 or an interfaced computing device. The type of processing depends upon the selected pump-probe spectroscopic technique.

Additional operations which may be associated with application 610 are further described in the Example, below. These include operations associated with adjusting the pump beam power/intensity during use of the pump-probe spectroscopy system and preventing the acquisition of image data associated with nonoptimal chopper phases.

The present pump-probe spectroscopy systems may be used in a variety of applications, including transient absorption spectroscopy, time-resolved infrared spectroscopy, reflectance transient absorption spectroscopy, femtosecond resolved stimulated Raman spectroscopy, or any other pump-probe spectroscopy making use of a modulated pump beam and a high speed dispersed detector. Regarding transient absorption spectroscopy, pump-probe pulse schemes for measuring and calculating changes in sample absorbance, such as those described in the following references may be used: Kanal, F. et al., "100-kHz shot-to-shot broadband data acquisition for high-repetition-rate pump-probe spectroscopy." *Optics Express*. Vol. 22, No. 14, Jul., 14, 2014, p. 16965 and Polack, T., et al., "CO Vibration as a Probe of Ligand Dissociation and Transfer in Myoglobin." *Physical Review Letters*. Vol. 93, No. 1, Jul. 1, 2004, p. 18102-1. Each of these references is hereby incorporated by reference in its entirety.

Advantages of at least some embodiments of the present pump-probe spectroscopy system include one or more of the following: broadband detection allows for the detection of all probe wavelengths simultaneously; an asynchronous chopper does not need to be synced to the laser (or vice versa); about 100% power transmission of the pump laser power through the chopper (compare this to acousto-optical modulation (AOM), which can have more than 60% loss in pump power in many situations); no complications with changing the pump wavelength as there is when using AOMs; the phase of chopper is locked and does not need to be set at the beginning of the experiment, which eliminates potential sources of experimental ambiguity; no down counting or other expensive/complicated (e.g., feedback loops) synchronization electronics are required; an inexpensive photodiode may be used to sync the camera to the chopper.

Finally, the present pump-probe spectroscopy systems allow any high repetition rate laser (e.g., 20 kHz-120 kHz) to be used to perform shot to shot pump probe spectroscopy and thus have the advantages of both high repetition and low repetition rate laser systems. Specifically, one can have the improved statistical averaging and lower pump pulse energies of high repetition rate lasers, but still retain the strong pulse to pulse correlations that have conventionally been acquired with low repetition rate lasers. This would allow spectroscopists to probe ever lower signals without damaging their samples, and to do it at a fraction of the cost and complexity of what it currently would take to perform these experiments.

EXAMPLE

This Example describes a data acquisition methodology in which broadband shot-to-shot differencing pump-probe spectroscopy is performed at very fast laser repetition rates (e.g., at least as high as 100 kHz). By shot-to-shot differencing it is meant that data is captured from every single probe laser pulse in the pulse sequence and is then compared to the next pulse in the sequence. This is by far the best way to acquire pump-probe data because it takes advantage of the strong intensity/spectral correlations that exist between pulses that are emitted close together in time. The further apart two pulses are in time when compared, the worse the correlations between the two are and the worse the resulting signal to noise ratio will be. Broadband (i.e., collecting multiple wavelengths simultaneously) shot-to-shot differencing has been widely used at lower repetition rates (up to a few kHz), but is very difficult at higher repetition rates for two main reasons.

The first reason is that one needs a camera/detector that is capable of recording data at least as fast as the repetition rate of the laser; otherwise one cannot capture each probe pulse's information individually. Fast single wavelength detectors are common, but commercially available line cameras are only just becoming available. The methodology of this Example utilizes one of the latter to acquire the entire spectra of the probe pulses for every single probe pulse in the pulse sequence (at repetition rates up to 120 kHz).

The second reason is that one needs to be able to modulate (i.e., block) a second laser beam at exactly half the repetition rate of the laser. This second beam is called the pump beam and is used to alter the state of a sample in some manner (e.g., photoexcitation) of interest. The probe beam is subsequently directed through the excited sample volume and then captured by the high-speed camera. Captured probe data is then compared between two conditions: when the pump is blocked and unblocked. Therefore, to be able to do shot-to-shot differencing, one needs the ability to efficiently block every other pump pulse in the laser pulse sequence. In the most common pump-probe experiment, transient absorption spectroscopy, this involves comparing the absorption spectra of the two probe pulses.

At slower repetition rates (~5 kHz or lower) shot-to-shot differencing is most commonly performed with a mechanical chopper acting as the pump modulation source, as this is the cheapest and most efficient method. For example, a 50% duty cycle fan blade may be electronically synchronized to spin at half the laser repetition frequency. When it spins, it blocks every other pump pulse in the sequence while letting the remaining pulses through unblocked. At higher laser repetition rates (e.g., 100 kHz), the moment of inertia of the spinning chopper blade is so high that short time adjustments to the spin rate become extremely difficult. The result is that the chopper cannot be synced perfectly to the laser repetition rate and there is a very large amount of phase jitter in the chopper blades (as much as 30%). Two groups have managed to perform shot-to-shot differencing at 100 kHz using a chopper to modulate their pump beam. (See Kanal, et. al and T. L Polack, et al., above.) Both methods require custom made synchronization electronics and/or use highly unusual triggering methods. For example, Kanal et al. used their chopper as the master clock which sends a signal to trigger the laser to emit a pulse rather than the usual method of the laser pulse output triggering the chopper. Aside from being unnecessarily complicated and expensive, many lasers cannot be triggered externally, so that technique would never work with them.

An alternative method for modulating a pump beam at high repetition rates involves acousto-optical modulation (AOM) instead of a chopper. It uses a specialized crystal and high-powered radio amplifier to diffract a portion of the pump beam at a desired frequency (up to MHz repetition rates). There is no phase drift/jitter with this technique, but it is quite expensive, difficult to use, and since the diffraction is not very efficient, a lot of the pump power (often over 60%) is lost.

The technique used in the present Example uses a high-speed chopper, but does not require any expensive extra electronics, complicated triggering methods, and there is no pump power loss. It is also very user friendly. Briefly, a commercially available high-speed chopper is run at half the laser repetition frequency using the chopper's internal clock drive. Because of this, it is completely unsynchronized to the laser and phase drift/jitter causes it to randomly go in and out of phase with the laser pulses. However, an inexpensive photodiode is used after the chopper to record the modulated pump beam. This photodiode signal is used to trigger the camera acquisition to start. Thus, the camera acquisition only starts when the chopper blade is in the correct phase to let the pump beam through. Therefore, the start of each camera acquisition is locked in phase with the chopper. If one were to continuously acquire data in this manner for a few seconds (i.e., the typical acquisition method), the chopper and laser would quickly walk out of phase with one another, and the resulting data would be useless. However, it has been determined that if one instead acquires in small sets of ~1,100 sequential probe pulses/images the chopper does not have a long enough time to walk out of phase and the pump pulses will be perfectly modulated over the entire acquisition time. At 100 kHz, 1,100 images are captured in 11 ms, which is only about 2.5 revolutions of the chopper blade. The acquisition of a set of sequential images is referred to herein as an "acquisition event" and the data associated with the acquisition event as "image data."

To acquire more images, the camera simply waits for the next trigger from the photodiode, and then acquires another set of 1,100 images. This can be repeated indefinitely until the desired signal to noise level is achieved. Furthermore, when capturing data at such a high frame rate, it has been determined that the time limiting step in the associated software is the speed in which the collected image data can be processed by the CPU. That is, the rate of image capture is higher than the rate of image processing. This is true both for acquiring images continuously and in small discrete sets. Therefore, there is very little time disadvantage in using the latter technique, and the same number of images can be captured and processed in roughly the same amount of time for both methods.

A schematic of the asynchronous chopping data acquisition methodology used in the present Example is illustrated in FIG. 1. Note that the optical layout shown is for a typical transient absorption experiment, but the methodology is relevant to any high repetition rate pump-probe experiment utilizing a broadband probe. Note also that for simplicity, only the laser amplifier is shown. In reality, additional optical elements (e.g. optical parametric amplifier, supercontinuum generation, etc.) may be used to convert the laser fundamental into the appropriate pump and probe beams.

The probe beam is directed onto a mechanical translation stage in order to be able to delay it relative to the pump beam and obtain time resolved data. Subsequent to the stage, the probe is directed onto the sample and then into a spectrometer, which disperses it into its component wavelengths. The dispersed beam is incident onto the high-speed line array camera (E2V, AViiVA® EM4). Individual image acquisitions from the camera are triggered by the connected frame grabber (National Instruments, PCIe 1430) installed in a generic PC, which is itself triggered by the master clock Trigger A ($\omega$=laser repetition rate) it receives from the laser amplifier. This master clock trigger sequence is either obtained from the "synchronization out" common on most commercial laser amplifiers, or it can be measured with an external photodiode if the laser does not have this output. Using this signal to trigger the camera ensures that individual images are only acquired when probe light is incident on the camera.

The pump beam is directed through a mechanical chopper (Scitec Instruments 310CD, 300D445 blade), which is being run off of its internal clock drive at half the repetition rate of the laser, $\omega$. Prior to the chopper, the pump beam is focused tightly at the plane of the chopper blade in order to ensure 100% transmission of the pump pulses through the small chopper apertures (0.34 mm). Note that in FIG. 1, lenses are used to focus and re-collimate the pump beam, but low dispersion mirrors could also be utilized to minimize the accumulation of chirp. After passing through the chopper, the pump pulse train is now modulated such that every other pulse is blocked. However, because the chopper is unsynchronized with the laser, this modulation is imperfect and will have phase drift/jitter issues. Therefore, a small fraction of the chopped pump beam is reflected off of a coverslip which directs it through a variable attenuator (e.g., a neutral density filter) and onto a photodiode. The majority of the pump that passes through the coverslip is then directed onto the sample volume that the probe is passing through. The pump fraction incident on the photodiode creates an analog electrical signal that is sent to the frame grabber and forwarded to the camera. This signal is used as a trigger (Trigger B) to signal the start an acquisition of 1,100 sequential pulses/images. Thus, the acquisition will only be started when the chopper blade phase is such that the pump pulse is unblocked. Consequently, each image sequence will be locked in phase with the others with the first image recorded always being with an unblocked pump pulse incident on the sample. Note that for the specific pump-probe spectroscopy system of FIG. 1, 1,100 was empirically determined to be the ideal sequence length in order to maximize the image capture/processing rate for this particular embodiment.

In order to ensure that partially blocked pump pulses do not trigger the start of an acquisition, the variable attenuator is set such that fully unblocked pump pulses are barely intense enough to create a photodiode signal that is above the trigger threshold of the frame grabber (see FIG. 2A). This also reduces random noise in the signal magnitude caused by long timescale (i.e., >>11 ms) fluctuations in the pump intensity. This is because when slow fluctuations downward in the pump intensity occur, no trigger signals strong enough to trigger the start of an acquisition event. Short time scale fluctuations in the pump intensity (<11 ms) will still be an issue because only the first pump pulse in the 1,100 pulse sequence is relevant to triggering the start of the acquisition. In order to collect more images, once an image sequence is fully captured, the software waits for the next appropriate photodiode trigger signal, and then captures another sequence while concurrently processing the previously captured images. This can be repeated as many times as desired until the desired signal to noise level is obtained. Using LabVIEW software to implement this technique, around 11,400 images will be captured and processed every second. However, using a computer with a faster processor can increase the number of images captured/processed per second, e.g., around 15,500 images captured/processed per second.

As noted above, in some cases, pump power/intensity may not be as stable as desired. In such cases, a self-corrective feedback loop may be used to counteract drifting pump power. The correction involves adjusting pump power during use of the pump-probe spectroscopy system of interest. To implement the correction/adjustment, a figure of merit range is measured for the system of interest. This figure of merit range will differ for different systems, but it is a measurable quantity. Specifically, for the system of interest at a fixed trigger threshold (i.e., a fixed predetermined threshold value), one measures and calculates the average time between acquisition events (i.e., the triggering/collection of a set number of sequential images, e.g., 1,100 images) at a low pump power (e.g., by adjusting the variable attenuator) and at a high pump power. At low pump power, the average time will be undesirably long (too little data being acquired) and at high pump power, the average time will be too short and too consistent (too much data being acquired). The ideal average time (ideal amount of data being acquired) should randomly fluctuate between the two average time extremes (randomly, since the average time depends upon the jitter of the chopper phase which is inherently random). The two average time extremes provide the figure of merit range for the system of interest.

During use of the pump-probe spectroscopy system of interest, the average time between acquisition events can be continually or periodically measured/calculated and compared to the figure of merit range. If the average time rises above the upper extreme of the figure of merit range (i.e., the average time is too long), the pump power can be increased (e.g., by adjusting the variable attenuator) to increase the number of acquisition events. If the calculated average time drops below the lower extreme of the figure of merit range (i.e., the average time is too short), the pump power can be decreased (e.g., by adjusting the variable attenuator) to decrease the number of acquisition events. A motorized variable attenuator may be used in order to facilitate these adjustments. It is noted that when the motorized variable attenuator is position as shown in FIG. 1 (after the coverslip that splits the pump beam into two paths), the self-corrective feedback loop described above counteracts pump power drifts affecting the triggering process. However, the motorized variable attenuator may also be placed prior to the coverslip so as to counteract pump power drifts that affect the magnitude of the pump-probe signal over time.

A data acquisition subsystem of the pump-probe spectroscopy system (see FIG. 6), e.g., via its application, can be configured to perform any of the operations described above (or associated operations), including the calculation of average times, the comparison to a figure of merit range and the adjustment of the variable attenuator.

Turning back to FIG. 2A-2C, as the chopper is being run unsynchronized to the laser and has significant jitter, there are three possible chopper phase conditions to consider which are outlined in these figures. Note that FIGS. 2A-2C do not represent the actual number of slots in the chopper blade (e.g., 445) and are for illustrative purposes only. The first condition is where a pump pulse happens to pass through the chopper blade near the center of the open aperture (FIG. 2A). This is the optimal situation because if this pulse creates a trigger that starts an acquisition event, the 11 ms timescale of the sequence acquisition is not long enough for the chopper phase drift/jitter to cause issues. The pump pulses are therefore perfectly modulated at half the repetition rate over the entire 11 ms image sequence acquisition. The second condition is when the phase of the chopper causes it to partially block a pump pulse (FIG. 2B). For the reasons outlined above, this situation cannot trigger the start of an image sequence, and nothing happens. Likewise, nothing will happen if the chopper fully blocks the pump pulse. The third condition (FIG. 2C) is when the phase of the chopper is such that the pump pulse that triggers the start of an acquisition is fully transmitted but happens to have passed very near the edge of the chopper blade. In this case, 11 ms is sometimes long enough for chopper phase drift to be an issue and the pump pulses may not be perfectly modulated across the image sequence. In practice, for the illustrative system of FIG. 1, the situation depicted in FIG.

2A happens in about 92.5±5% of the captured image sequences, and the situation depicted in FIG. 2C about 7.5% of time.

Turning to FIGS. 3A-3B, these figures demonstrate why it is not beneficial to focus the pump beam extremely tightly in the plane of the chopper as one might expect. Using relatively large focused spot sizes results in pump pulses near the edge of the chopper blade being partially clipped. This makes their Trigger B signals too weak to start an acquisition event. Therefore, focusing to a relatively large beam diameter forces more image sequence acquisitions to be triggered in condition A (FIG. 2A). This is counteracted by the fact that larger beam diameters reduce the chopper phase window in which the pump is fully transmitted. Thus, with large beam diameters, phase drift is more likely to cause some improperly modulated pump pulses over the course of the 11 ms acquisition even when the first pump pulse that triggers the acquisition is not near the edge of the blades. These two effects compete and the optimal focal spot size which balances the two effects can be empirically determined. For the illustrative embodiment of FIG. 1, it was determined that a spot size of about 50 μm in diameter results in the highest fraction of pump pulse sequences being perfectly modulated.

Regardless of the type of pump-probe experiment, triggering in condition C (FIG. 2C) will always cause a reduction in the overall signal amplitude relative to condition A (FIG. 2A). However, an efficient real time algorithm can be utilized to identify and disregard flawed data that was acquired in condition C. The exact details of the algorithm will be different for each type of pump probe experiment but are based on comparing the overall signal magnitude obtained from each image sequence to the sequences with the largest signal magnitudes. All sequences with signals under a certain threshold would be discarded.

Unfortunately, disregarding data will always slow the data acquisition down somewhat. However, as can be seen in FIGS. 3A-3B, the ~7.5% increase in acquisition time with the above methodology is clearly worth the effort as compared to chopping at a slower rate where phase drift/jitter is not an issue.

As noted above, some data may be acquired under nonoptimal chopper phase conditions (e.g., FIG. 2C) and it may be desirable to discard such data. Instead of discarding data, the ratio of optimal data acquired (data acquired under optimal chopper phase conditions (e.g., FIG. 2A)) to nonoptimal data acquired, the following technique may be used. The technique involves rejecting trigger signals associated with nonoptimal chopper phase conditions, thereby preventing acquisition events under such nonoptimal chopper phase conditions.

The technique is illustrated in FIGS. 8A-8D. As shown in the top panel, a transistor-transistor logic (TTL) signal from the "sync-out" port of the chopper is digitized by a data acquisition device (DAQ). This TTL signal indicates the phase of the chopper in real time. The digitized TTL signal has information about the timing of the rise ($R_1$, $R_2$, $R_3$), the timing of the fall ($F_1$, $F_2$, $F_3$) and the width ($W_1$, $W_2$, $W_3$) of the original, analog TTL signal. The digitized TTL signal may be received by the data acquisition subsystem (see FIG. 6) as another input. As illustrated in FIGS. 8A-8C, the rise (or fall) times of the digitized TTL signal may be compared to the timing of the trigger signal received from the photodiode monitoring the pump beam. A determination may be made whether to reject the trigger signal, thereby preventing acquisition of data, or whether to accept the trigger signal, thereby initiating acquisition of data. The comparison/determination may be based on predetermined time difference thresholds, e.g., reject when the time difference between a rise (or a fall) and the trigger signal is less than a particular value, otherwise accept. In addition, as illustrated in FIG. 8D, the width of the digitized TTL signal may be monitored over time. Rapidly changing widths over a particular period of time can indicate chopper drift/jitter. A determination may be made whether to reject one or more trigger signals over this period of time, thereby preventing acquisition of data, or whether to accept the one or more trigger signals, thereby initiating acquisition of data. The comparison/determination may be based on a predetermined width value, e.g., one representing a stable width. The data acquisition subsystem, via its application, can be configured to perform any of the operations described above (or associated operations).

Finally, FIGS. 4A-4C compares the stability of baseline transient absorption data when chopped at different rates using a commercial 100 kHz amplifier (Spectra Physics, Spirit 1040-4). In this example data, the pump beam is being blocked before reaching the sample; therefore, no transient absorption signal should be present and a perfectly flat baseline should be observed. The probe beam in this example data was created by focusing ~3 μJ pulses of the 1040 nm fundamental with a 250 mm focal length lens into a 4 mm thick undoped YAG crystal to create a spectrally broadened supercontinuum. FIGS. 4A and 4B show the magnitudes of the transient absorption signal baselines when chopping at 250 Hz and 1 kHz, respectively. Each spectrum shown represents the "signal" calculated from a single 1,100 image sequence. At both of these conventional chopping rates, the baseline is clearly not flat because 100 kHz probe pulses are no longer strongly correlated on these chopping time scales. In fact, one can clearly see echoes of the probe spectrum bleeding through. When compared to the data captured with the methodology described above (FIG. 4C) there is no bleed through whatsoever of the probe spectrum. Acquiring/processing for five seconds per data point results in a nearly perfectly flat baseline with a standard deviation noise level fluctuation of $\sim 3.5 \times 10^{-6}$ optical density (calculated over 100 data points at 600 nm). This is 5.7 times lower than the noise level of the industry leading HARPIA spectrometer from Light Conversion, which can only chop the pump beam at a few kHz.

The word "predetermined" is used herein to refer to a value that is established in advance, prior to carrying out the steps of the disclosed methods.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A pump-probe spectroscopy system comprising:
an optical subsystem comprising a light source and optical elements for generating a pulsed pump beam and a pulsed probe beam, the pulsed probe beam having a probe pulse frequency ω of at least 20 kHz;
a detector subsystem configured to detect a sample signal induced by the pulsed pump beam and the pulsed probe beam;
a chopper configured to adjust the frequency of the pump beam to ω/2, wherein the chopper is synchronized with a detector of the detector subsystem but is unsynchronized with the pulsed probe beam; and
a data acquisition subsystem comprising a processor and a non-transitory computer-readable medium comprising instructions, that, when executed by the processor, cause the system to initiate acquisition of image data by the detector based on a trigger signal derived from the pulsed pump beam.

2. The system of claim 1, wherein the pulsed probe beam is a pulsed broadband probe beam.

3. The system of claim 1, wherein the probe pulse frequency ω is at least 100 kHz.

4. The system of claim 1, wherein the image data is a predetermined number of sequential images.

5. The system of claim 1, the non-transitory computer-readable medium comprising instructions, that, when executed by the processor, cause the system to
receive a second trigger signal derived from the pulsed probe beam and output the second trigger signal to the detector;
receive the trigger signal derived from the pulsed pump beam;
determine if the trigger signal derived from the pulsed pump beam meets or exceeds a predetermined threshold value; and
initiate the acquisition of image data if the trigger signal derived from the pulsed pump beam meets or exceeds the predetermined threshold value.

6. The system of claim 5, the non-transitory computer-readable medium comprising instructions, that, when executed by the processor, cause the system to
calculate an average time between the acquisition of image data;
determine if the average time is within a figure of merit range for the system; and
adjust the pulsed pump beam's intensity if the average time is outside the figure of merit range.

7. The system of claim 5, the non-transitory computer-readable medium comprising instructions, that, when executed by the processor, cause the system to
receive a third trigger signal derived from the chopper;
determine if a time difference between the trigger signal derived from the pulsed pump beam and the third trigger signal meets or exceeds a predetermined time difference threshold; and
initiate the acquisition of image data if the time difference meets or exceeds the predetermined time difference threshold.

8. A method for performing pump-probe spectroscopy, the method comprising:
illuminating a sample mounted on the system of claim 1 with the pulsed pump beam and the pulsed probe beam to induce the sample signal; and
initiating the acquisition of image data by the detector.

9. A pump-probe spectroscopy system comprising:
a processor; and
a non-transitory computer-readable medium comprising instructions, that, when executed by the processor, cause the system to
receive a first trigger signal derived from a pulsed probe beam having a probe pulse frequency ω and output the first trigger signal to a detector;
receive a second trigger signal derived from a pulsed pump beam having a pump pulse frequency ω/2, the second trigger signal operably coupled to the detector;
determine if the second trigger signal meets or exceeds a predetermined threshold value; and
initiate acquisition of image data by the detector if the second trigger signal meets or exceeds the predetermined threshold value.

10. The system of claim 9, the non-transitory computer-readable medium comprising instructions, that, when executed by the processor, cause the system to
calculate an average time between the acquisition of image data;
determine if the average time is within a figure of merit range for the system; and
adjust the pulsed pump beam's intensity if the average time is outside the figure of merit range.

11. The system of claim 9, the non-transitory computer-readable medium comprising instructions, that, when executed by the processor, cause the system to
receive a third trigger signal derived from a chopper configured to provide the pulsed pump beam's frequency ω/2;
determine if a time difference between the second trigger signal and the third trigger signal meets or exceeds a predetermined time difference threshold; and
initiate the acquisition of image data if the time difference meets or exceeds the predetermined time difference threshold.

12. A non-transitory computer-readable medium comprising instructions, that, when executed by a processor, cause a pump-probe spectroscopy system to
receive a first trigger signal derived from a pulsed probe beam having a probe pulse frequency co and output the first trigger signal to a detector;
receive a second trigger signal derived from a pulsed pump beam having a pump pulse frequency ω/2, the second trigger signal operably coupled to the detector;
determine if the second trigger signal meets or exceeds a predetermined threshold value; and
initiate acquisition of image data by the detector if the second trigger signal meets or exceeds the predetermined threshold value.

13. The non-transitory computer-readable medium of claim 12, comprising instructions, that, when executed by the processor, cause the pump-probe spectroscopy system to
calculate an average time between the acquisition of image data;
determine if the average time is within a figure of merit range for the system; and
adjust the pulsed pump beam's intensity if the average time is outside the figure of merit range.

14. The non-transitory computer-readable medium of claim 12, comprising instructions, that, when executed by the processor, cause the pump-probe spectroscopy system to
receive a third trigger signal derived from a chopper configured to provide the pulsed pump beam's frequency ω/2;

determine if a time difference between the second trigger signal and the third trigger signal meets or exceeds a predetermined time difference threshold; and initiate the acquisition of image data if the time difference meets or exceeds the predetermined time difference threshold.

15. A method for performing pump-probe spectroscopy, the method comprising:

receiving, by a processor, a first trigger signal derived from a pulsed probe beam having a probe pulse frequency $\omega$ and outputting the first trigger signal to a detector;

receiving, by the processor, a second trigger signal derived from a pulsed pump beam having a pump pulse frequency $\omega/2$, the second trigger signal operably coupled to the detector;

determining, by the processor, if the second trigger signal meets or exceeds a predetermined threshold value; and initiating acquisition of image data by the detector if the second trigger signal meets or exceeds the predetermined threshold value.

* * * * *